United States Patent
Ding et al.

(10) Patent No.: US 11,033,896 B2
(45) Date of Patent: Jun. 15, 2021

(54) LATERAL-FLOW ASSAY DEVICE WITH FILTRATION FLOW CONTROL

(71) Applicant: Ortho-Clinical Diagnostics, Inc., Raritan, NJ (US)

(72) Inventors: Zhong Ding, Pittsford, NY (US); Edward R. Scalice, Penfield, NY (US); Philip C. Hosimer, Rochester, NY (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 1010 days.

(21) Appl. No.: 14/817,946

(22) Filed: Aug. 4, 2015

(65) Prior Publication Data
US 2016/0038937 A1    Feb. 11, 2016

Related U.S. Application Data

(60) Provisional application No. 62/034,830, filed on Aug. 8, 2014.

(51) Int. Cl.
*B01L 3/00* (2006.01)
*G01N 33/558* (2006.01)

(52) U.S. Cl.
CPC .......... *B01L 3/5023* (2013.01); *G01N 33/558* (2013.01); *B01L 2300/0681* (2013.01); *B01L 2400/0406* (2013.01)

(58) Field of Classification Search
CPC .......... B01L 3/5023; B01L 2400/0406; B01L 2300/0681; G01N 33/558
See application file for complete search history.

(56) References Cited

U.S. PATENT DOCUMENTS

| | | | |
|---|---|---|---|
| 4,287,155 A | 9/1981 | Tersteeg et al. | |
| 5,120,643 A | 6/1992 | Ching et al. | |
| 5,559,041 A | 9/1996 | Kang et al. | |
| 5,607,863 A | 3/1997 | Chandler | |
| 5,714,389 A | 2/1998 | Charlton et al. | |
| 5,869,004 A | 2/1999 | Parce et al. | |
| 6,048,498 A | 4/2000 | Kennedy | |
| 6,139,800 A | 10/2000 | Chandler | |
| 6,228,660 B1 | 5/2001 | May et al. | |
| 6,241,886 B1 | 6/2001 | Kitagawa et al. | |
| 6,270,641 B1 | 8/2001 | Griffiths et al. | |
| 6,372,542 B1 | 4/2002 | Martin et al. | |
| 6,402,300 B1 | 6/2002 | Silverbrook | |
| 6,451,264 B1 | 9/2002 | Bhullar et al. | |
| 6,733,682 B1 | 5/2004 | Björkman et al. | |
| 6,776,965 B2 | 8/2004 | Wyzgol et al. | |
| 6,811,736 B1 | 11/2004 | Ohman et al. | |
| 6,884,370 B2 | 4/2005 | Ohman et al. | |
| 6,896,358 B1 | 5/2005 | Silverbrook | |
| 7,005,301 B2 | 2/2006 | Cummings et al. | |
| 7,032,992 B2 | 4/2006 | Silverbrook | |
| 7,132,078 B2 | 11/2006 | Rawson et al. | |
| RE39,664 E | 5/2007 | Gordon et al. | |
| 7,267,423 B2 | 9/2007 | Silverbrook | |
| 7,312,084 B2 | 12/2007 | Jakubowicz et al. | |
| 7,416,700 B2 | 8/2008 | Buechler et al. | |
| 7,503,954 B2 | 3/2009 | Haefner et al. | |
| 7,581,817 B2 | 9/2009 | Silverbrook | |
| 7,632,468 B2 | 12/2009 | Barski et al. | |
| 7,654,643 B2 | 2/2010 | Silverbrook | |
| 7,816,122 B2 | 10/2010 | Clark et al. | |
| 7,819,507 B2 | 10/2010 | Brown et al. | |
| 7,883,183 B2 | 2/2011 | Silverbrook | |
| 7,891,769 B2 | 2/2011 | Silverbrook | |
| 7,984,968 B2 | 7/2011 | Silverbrook | |
| 8,025,854 B2 | 9/2011 | Ohman et al. | |
| 8,043,562 B2 | 10/2011 | Tomasso et al. | |
| 8,080,204 B2 | 12/2011 | Ryan et al. | |
| 8,821,812 B2 | 9/2014 | Öhman et al. | |
| 2003/0022380 A1 | 1/2003 | Jakubowicz et al. | |
| 2004/0072367 A1 | 4/2004 | Ding et al. | |

(Continued)

FOREIGN PATENT DOCUMENTS

| CN | 2264914 Y | 10/1997 |
|---|---|---|
| CN | 103270150 A | 8/2013 |

(Continued)

OTHER PUBLICATIONS

Canadian Office Action and Examination Search Report for CA 2,957,728; dated May 29, 2017; 6 pages.

(Continued)

*Primary Examiner* — Andrea S Grossman
(74) *Attorney, Agent, or Firm* — K&L Gates LLP; Louis C. Cullman; Brian J. Novak

(57) ABSTRACT

A lateral-flow assay device includes a substrate with a sample addition zone and a fluid flow path. A cover supports a filter having a portion contacting the substrate to create a contact area that at least partly overlaps the sample addition zone. Another portion extends from the contact portion to the supported periphery of the filter to define with the substrate a reservoir configured to retain the filtrate by capillary pressure between the substrate and the extending portion. The reservoir volume is based on an acute angle formed between the substrate and the extending portion of the filter and on a fluid meniscus of the filtrate. The filter and sample addition zone are configured to provide capillary pressure drawing the filtrate from the reservoir to the sample addition zone. Methods for controlling flow characteristics in a lateral-flow assay device are also described.

17 Claims, 7 Drawing Sheets

(56) References Cited

U.S. PATENT DOCUMENTS

| | | |
|---|---|---|
| 2005/0116990 A1 | 6/2005 | Silverbrook |
| 2006/0019265 A1 | 1/2006 | Song et al. |
| 2006/0205086 A1 | 9/2006 | Hu |
| 2006/0239859 A1 | 10/2006 | Ohman et al. |
| 2006/0289787 A1 | 12/2006 | Ohman et al. |
| 2007/0231883 A1 | 10/2007 | Lindstrom et al. |
| 2007/0268328 A1 | 11/2007 | Silverbrook |
| 2009/0068061 A1 | 3/2009 | Chen |
| 2010/0176050 A1 | 7/2010 | Mori |
| 2011/0011781 A1 | 1/2011 | Blankenstein et al. |
| 2013/0112612 A1 | 5/2013 | Blankenstein et al. |
| 2013/0330713 A1 | 12/2013 | Jakubowicz et al. |
| 2014/0141527 A1 | 5/2014 | Ding et al. |
| 2015/0153258 A1 | 6/2015 | Huemer |
| 2017/0059460 A1 | 3/2017 | Jeon et al. |

FOREIGN PATENT DOCUMENTS

| | | |
|---|---|---|
| EP | 0 057 110 A2 | 8/1982 |
| EP | 0 920 356 B1 | 12/2002 |
| EP | 1 292 449 B1 | 10/2008 |
| EP | 2 695 656 A1 | 2/2014 |
| WO | WO 99/32884 | 7/1999 |
| WO | WO 03/103835 A1 | 12/2003 |
| WO | WO 2005/089082 A2 | 9/2005 |
| WO | WO 2005/118139 A1 | 12/2005 |
| WO | WO 2006/137785 A1 | 12/2006 |
| WO | WO 2007/149042 A1 | 12/2007 |
| WO | WO 2013/154946 A1 | 10/2013 |

OTHER PUBLICATIONS

International Search Report and Written Opinion for PCT/US2015/043769; dated Sep. 23, 2015; 7 pages.

U.S. Appl. No. 62/035,083, filed Aug. 8, 2014; Title: Lateral Flow Assay Device; 75 pages.

Chinese Office Action and Search Report for CN 201580054668.7; dated Sep. 21, 2017; 15 pages.

Russian Office Action and Search Report for RU 2017107195; dated Oct. 16, 2017; 19 pages.

210  648  710

710  648  210

LATERAL-FLOW ASSAY DEVICE WITH FILTRATION FLOW CONTROL

CROSS REFERENCE TO RELATED APPLICATION(S)

This application claims priority under applicable portions of 35 U.S.C. § 119 to U.S. Patent Application Ser. No. 62/034,830, filed Aug. 8, 2014, and entitled: LATERAL-FLOW ASSAY DEVICE WITH FILTRATION FLOW CONTROL, the entire contents of which are incorporated by reference herein.

TECHNICAL FIELD

This application relates to the field of clinical diagnostics and more specifically to a lateral-flow assay device.

BACKGROUND

The use of diagnostic assays is very well known for the diagnosis, treatment and management of many diseases. In that regard, different types of diagnostic assays have been developed to simplify the detection of various analytes in clinical samples such as blood, serum, plasma, urine, saliva, tissue biopsies, stool, sputum, skin or throat swabs and tissue samples or processed tissue samples. These assays are frequently expected to provide a fast and reliable result, while being easy to use and inexpensive to manufacture.

One common type of disposable assay device includes a sample addition zone or area for receiving the liquid sample, at least one reagent zone, a reaction zone (also known as a detection zone), and optionally an absorbing zone. These zones can be arranged in order along a fluid passage or channel. These assay devices, commonly known as lateral test strips, can employ a porous material, e.g., nitrocellulose, defining a path for fluid capable of supporting capillary flow. Examples include those devices shown in U.S. Pat. Nos. 5,559,041, 5,714,389, 5,120,643, and 6,228,660, all of which are incorporated herein by reference in their entireties.

The sample addition zone of these assay devices frequently includes a porous material, capable of absorbing the liquid sample, and, when separation of blood cells is required, also effective to trap the red blood cells. Examples of such materials are polymeric membrane filters or fibrous materials, such as paper, fleece, or tissue, comprising e.g., cellulose, wool, glass fiber, asbestos, synthetic fibers, polymers, or mixtures of the same.

Another type of lateral-flow assay device is defined by a non-porous substrate having a plurality of upwardly extending microposts (also referred to as "micropillars" or "projections"). The microposts are defined dimensionally and in terms of their spacing to produce spontaneous capillary flow when a liquid is introduced. Examples of such devices are disclosed in U.S. Pat. No. 8,025,854B2, WO 2003/103835, WO 2005/089082, WO 2005/118139 and WO 2006/137785, all of which are incorporated by reference herein in their entireties.

A known non-porous assay device of the above type is shown in FIG. 1. The assay device 1 has at least one sample addition zone 2, a reagent zone 3, at least one detection zone 4, and at least one wicking zone 5, each disposed on a common substrate 9. These zones are aligned along a defined flow path by which sample flows from the sample addition zone 2 to the wicking zone 5 under the influence of capillary pressure provided between microposts 7. Capture elements, such as antibodies, can be supported in the detection zone 4, these elements being capable of binding to an analyte of interest, the capture elements being deposited on the device, e.g., by coating. In addition, a labeled conjugate material, also capable of participating in reactions that will enable determination of the concentration of the analyte, is separately deposited on the device in the reagent zone 3, wherein the conjugate material carries a label for detection in the detection zone 4 of the assay device 1.

The conjugate material is gradually dissolved as the sample flows through the reagent zone, forming a conjugate plume of dissolved labeled conjugate material and sample that flows downstream along the defined flow path of the device 1 to the detection zone 4. As the conjugate plume flows into the detection zone 4, the conjugated material will be captured by the capture elements such as via a complex of conjugated material and analyte (e.g., as in a "sandwich" assay) or directly (e.g., as in a "competitive" assay). Unbound dissolved conjugate material will be swept past the detection zone 4 and into the wicking zone 5.

An instrument such as that disclosed in U.S. 2006/0289787A1, U.S. 2007/0231883A1, U.S. Pat. Nos. 7,416,700 and 6,139,800, all incorporated by reference in their entireties herein, is configured to detect the bound conjugated material in the detection zone 4. Common labels include fluorescent dyes that can be detected by instruments which excite the fluorescent dyes and incorporate a detector capable of detecting the resulting fluorescence.

In the foregoing devices and in the conduction of assays, the resulting level of signal in the detection zone is read using a suitable detection instrument after the conjugate material has been dissolved and sample and unbound conjugate material and, optionally, wash fluid added to a reagent zone 3 of the device 1 has reached and subsequently filled the wicking zone 5 of the device 1.

In point of care (POC) applications, there is a continuing desire to reduce the volume of sample aliquots (e.g., to use 25 µL instead of 200 µL samples). For many assays, however, small sample volume leads to undesirable lower sensitivity. To increase the sensitivity at these lower sample volumes, it is important to increase plasma yield, i.e., the percentage of the sample aliquot that reaches the reagent zone 3. There is therefore a need to provide a device capable of dispensing micro-volumes of sample with an improved yield of plasma or other fluid of interest.

BRIEF DESCRIPTION

In an exemplary lateral-flow assay device, a concave-shaped filter is used over the sample addition zone and partly in contact therewith. The filter can be peripherally supported by a cover of the device. It has been determined that a fluid meniscus is produced between the filter and the sample addition zone. Specifically, fluid is retained by capillary pressure between the filter and the sample addition zone in various configurations. It has further been determined that the size of the meniscus is controlled by the filtration rate, the channel flow rate and the geometry of the filter, particularly through control of an angle α, which is subtended between the filter and the top surface of the substrate of the assay device directly beneath the sample addition zone of the device, the contact area, and the size of the sample addition zone.

It is desirable to retain the meniscus within a selected region of the assay device. Preventing the meniscus from, e.g., becoming oversized and reaching beyond the peripheral support of the filter to the underside of the cover advantageously reduces the probability of fluid becoming unavailable to flow into the reagent zone. This objective can only be realized by a proper design relating the size of the sample addition zone, the contact area of the sample and the geometry of the filter for a given sample size. Such a design can advantageously provide improved yield of a fluid being tested, permitting the use of smaller sample volumes.

Therefore and according to one aspect, there is provided a lateral-flow assay device for a sample, the device comprising: a substrate having a sample addition zone and a fluid flow path through which a filtrate flows under capillary action away from said sample addition zone; a cover arranged over the substrate and having an aperture defining a metering port configured to receive the sample; and a filter supported peripherally within the aperture and configured to permit at least a portion of the sample to pass therethrough as the filtrate, the supported filter having: at least one contact portion in direct contact with the substrate to create a contact area that at least partly overlaps the sample addition zone; and another portion that extends from the at least one contact portion to the supported periphery of the filter to define with the substrate a reservoir configured to retain the filtrate by capillary pressure between the substrate and the extending portion of the filter, wherein the reservoir has a volume based on an acute angle formed between the substrate and the extending portion of the filter and based on a fluid meniscus of the filtrate, and the filter and sample addition zone are configured to provide a capillary pressure drawing the filtrate from the reservoir to the sample addition zone.

According to another aspect, there is provided a method for controlling flow characteristics in a lateral-flow assay device, the device comprising a cover and a substrate, the cover having an aperture configured to receive a sample and peripherally supporting a filter, and the substrate having a sample addition zone and a fluid flow path through which a filtrate flows under capillary action away from the sample addition zone, the method comprising: adding a selected quantity of a sample via the aperture; and disposing at least one portion of the filter into contact with the substrate at least partly over the sample addition zone, so that the filtrate passes through the filter from the sample at a first flow rate and is retained by capillary pressure in a volume between the substrate and an extending hydrophilic portion of the filter spaced apart from the substrate and extending to an outer periphery of the supported filter, in which the filtrate is drawn by capillary pressure from the volume into the sample addition zone at a second flow rate slower than the first flow rate; wherein the quantity of the sample is based on the first and second flow rates and on a limit of the volume, the limit determined by at least one angle subtended between the substrate and the extending hydrophilic portion of the filter.

According to still another aspect, there is provided a method for controlling flow characteristics in a lateral-flow assay device, the device comprising a cover and a substrate, the cover having an aperture configured to receive a sample and peripherally supporting a filter, and the substrate having a sample addition zone and a fluid flow path through which a filtrate flows under capillary action away from the sample addition zone, the method comprising: adding a selected quantity of a sample via the aperture; and pressing at least one portion of the filter into contact with the substrate at least partly over the sample addition zone using at least one projecting member of the cover so that at least one angle is defined, the at least one angle subtended between the substrate and a hydrophilic portion of the filter spaced apart from the substrate and extending to an outer periphery of the supported filter, wherein the filtrate passes through the filter from the sample at a first flow rate and is retained by capillary pressure in a volume between the substrate and the hydrophilic portion, in which the filtrate is drawn by capillary pressure from the volume into the sample addition zone at a second flow rate slower than the first flow rate; wherein the quantity of the sample is based on the first and second flow rates and on the at least one angle.

One advantage realized is that faster and more reliable flow can be achieved of an applied sample to a lateral-flow assay device due to better control of filtration rate and reduced chance of fluid reaching at or even beyond the supported edge of the filter. As a result, capillary pressure (e.g. negative capillary pressure) between the filter and the assay device is of a magnitude sufficient to provide an effective driving force for filtration but not so large that it might interfere with the flow of fluid along a fluid flow path leading away from the sample addition zone of the device. In addition, the angle $\alpha$ between the filter and the assay device can control the meniscus size and the capillary pressure.

Another advantage is that of improved filtration efficiency and plasma yield for performing an assay due to at least: i) a smaller filter traps less plasma as waste inside the filter; ii) capillary pressure due to the smaller geometry between the filter and the surface of the assay device increases the driving force for faster filtration; or iii) a smaller sample zone traps less sample fluid in the micropost matrix of the assay device since there is no need to apply another porous pad under the filter to drive filtration. Various configurations described herein can provide a significantly higher plasma yield as compared to other known assay device designs.

Yet another advantage is that the defined fluid/filtrate meniscus has a number of beneficial functions including that of offering a stable fluid supply for the channel flow through the various zones of the lateral-flow assay device. The size of the meniscus may differ depending on a sample hematocrit level or sample volume, but its capillary pressure remains small compared to a capillary pressure in the flow channel or the wicking zone, resulting in a generally constant flow rate during fluid flow (indicated by a constant flow rate after fluid reaches the wicking zone 5 while the meniscus is shrinking in size).

Still further, the shape of the filter as well as the geometries of the sample zone and the contact area can be very flexible. According to at least one version, these features may be round or form other polygonal shapes (e.g., elliptical, rectangular, etc). Still further, the sample zone edge can be used to "pin" the meniscus and therefore can contribute to define the shape and size of the edge of the sample addition zone.

These and other features and advantages of various embodiments, variations, and modifications will be readily apparent from the following Detailed Description, which should be read in conjunction with the accompanying drawings.

DETAILED DESCRIPTION

Figure 1:
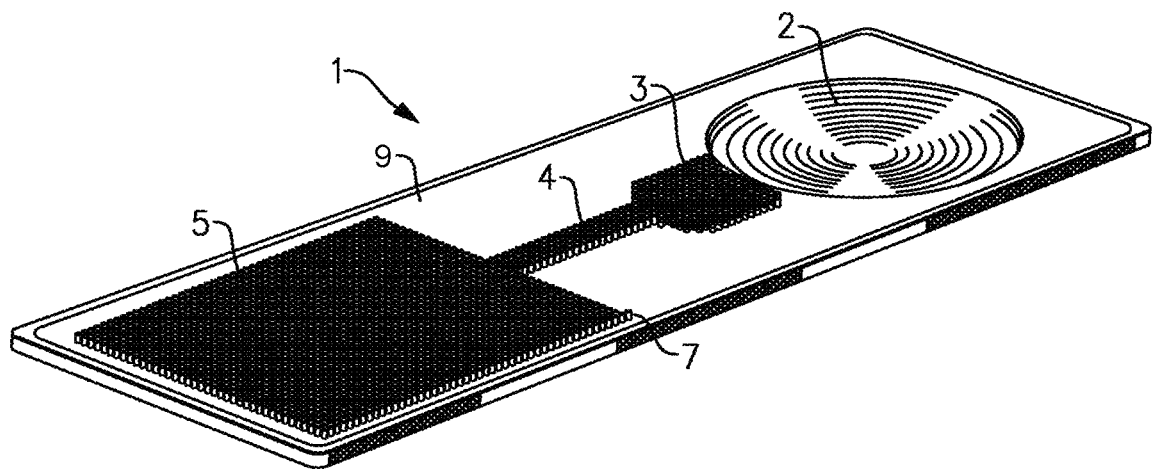
FIG. 1 is a perspective view of a known lateral-flow assay device.

The following description relates to certain embodiments for a filter design for a lateral-flow assay device. It will be readily apparent that the embodiments described herein are intended to be merely exemplary and therefore numerous other variations and modifications are possible. In addition, several terms are used throughout the following discussion such as "first", "second", "above", "below", "top", "bottom", "lateral" and the like for purposes of providing a suitable frame of reference in regard to the accompanying drawings. To that end, these terms should not be regarded as being overly restrictive in terms of the scope of the described apparatus and methods, unless otherwise specifically indicated herein.

It should further be noted that the accompanying drawings are not necessarily presented to scale and therefore no narrowing interpretation should be made in terms of dimensions that have been depicted.

As used in this specification and the appended claims, the singular forms "a", "an" and "the" are intended to further include plural referents unless the context clearly dictates otherwise.

The term "about" as used in connection with a numerical value throughout the description and the claims denotes an interval of accuracy, familiar and acceptable to a person skilled in the art. The interval governing this term is preferably ±30%.

In terms of defining certain of the terms that follow, the term "analyte" is used as a synonym of the term "marker" and intended to minimally encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The term "sample" herein means a volume of a liquid, solution or suspension, intended to be subjected to qualitative or quantitative determination of any of its properties, such as the presence or absence of a component, the concentration of a component, etc. Typical samples in the context of the present invention as described herein are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples, but preferably to samples of whole blood, urine or sputum.

In other instances, the sample can be related to food testing, environmental testing, bio-threat or bio-hazard testing, etc. This represents only a small example of samples that can be used in the present invention.

In the present invention, the determination based on lateral flow of a sample and the interaction of components present in the sample with reagents present in the device or added to the device during the procedure and detection of such interaction, either quantitatively or qualitatively, may be for any purpose, such as diagnostic purposes. Such tests are often referred to as "lateral-flow assays".

Examples of diagnostic determinations include, but are not limited to, the determination of analytes, also called markers, specific for different disorders, e.g., chronic metabolic disorders, such as blood glucose, blood ketones, urine glucose (diabetes), blood cholesterol (atherosclerosis, obesity, etc.); markers of other specific diseases, e.g., acute diseases, such as cardiac coronary infarct markers (e.g., troponin I, troponin-T, NT-proBNP), markers of thyroid function (e.g., determination of thyroid stimulating hormone (TSH)), markers of viral infections (e.g., the use of lateral-flow immunoassays for the detection of specific viral antibodies), etc.

Yet another important field is the field of companion diagnostics in which a therapeutic agent, such as a drug, is administered to an individual in need of such a drug. An appropriate assay is then conducted to determine the level of an appropriate marker to determine whether the drug is having its desired effect. Alternatively, the assay device usable with the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites in a urine or other sample.

The term "lateral-flow assay device", as discussed herein refers to any device that receives fluid, such as at least one sample, such as a bodily fluid sample, and includes at least one laterally disposed fluid transport or flow path along which various stations or sites (zones) are provided for supporting various reagents, filters and the like through which sample traverses under the influence of capillary or other applied forces and in which lateral-flow assays are conducted for the detection of at least one analyte of interest.

The terms "automated clinical analyzer", "clinical diagnostic apparatus" or "clinical analyzer" as discussed herein, refer to any apparatus enabling the scheduling and processing of various analytical test elements, including lateral-flow assay devices, as discussed herein and in which a plurality of test elements can be initially loaded for processing. This apparatus further includes a plurality of components/systems configured for loading, incubating and testing/evaluating a plurality of analytical test elements in automated or semi-automated fashion and in which test elements are automatically dispensed from at least one contained storage supply, such as a cartridge, without user intervention.

The term "testing apparatus" refers to any device or analytical system that enables the support, scheduling and processing of lateral-flow assay devices. A testing apparatus can include an automated clinical analyzer or clinical diagnostic apparatus such as a bench, table-top or main frame clinical analyzer, as well as point of care and other suitable devices. For purposes of this definition, the testing apparatus may include a plurality of components/systems for loading and testing/evaluating of at least one lateral-flow assay device including detection instruments for detecting the presence of at least one detectable signal of the assay device.

The terms "zone", "area" and "site" are interchangeably used in the context of this description, examples and claims to define parts of a fluid flow path on an assay device, either in prior art devices or according to an embodiment described herein, including devices in which a sample is first applied to the device and then subsequently directed. The term "reaction" is used to refer to any interaction that takes place between components of a sample and reagent(s) on or in the substrate, or between two or more components present in the sample. The term "reaction" is in particular used to define a reaction taking place between an analyte and a reagent as part of the qualitative or quantitative determination of the analyte.

The terms "substrate" or "support" refers to the carrier or matrix to which a sample is added, and on or in which the determination is performed, or where the reaction between analyte and reagent takes place.

The term "detection" and "detection signal" refers herein to the ability to provide a perceivable indicator that can be monitored either visually and/or by machine vision such as a detection instrument (e.g., a fluorimeter, reflectometer or other suitable device).

The term "process-related event" refers herein to an event that occurs prior to the detection of analyte in a lateral-flow assay device, such as, for example, the addition of at least one reagent.

Figure 2:
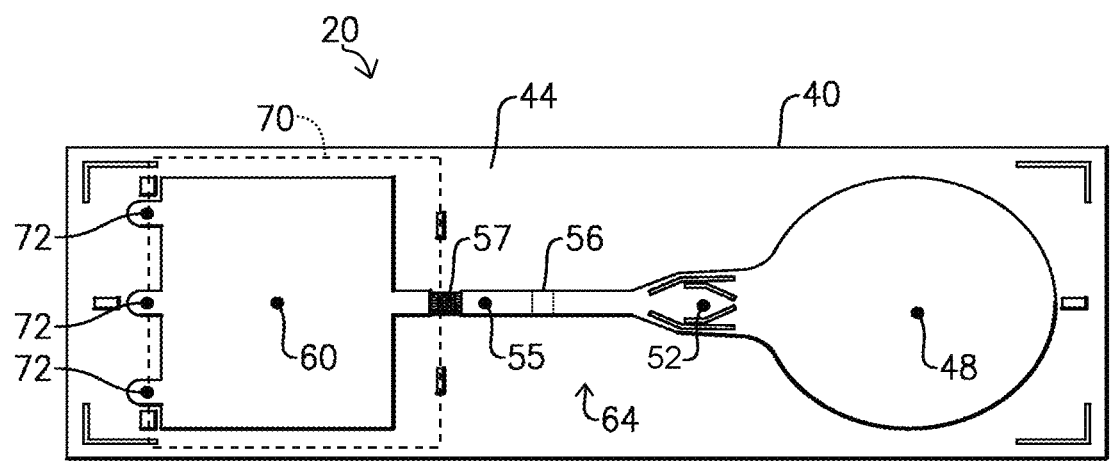
FIG. 2 is a plan view of another known lateral-flow assay device.

Referring to FIG. 2, there is shown one version of a lateral-flow assay device 20, the device including a planar substrate 40 which can be made from a moldable plastic or other suitable non-porous material. Further details of this and related devices are described below and in U.S. Patent Application Publication No. 2014/0141527 A1, entitled "Quality/Process Control of a Lateral-flow Assay Device Based on Flow Monitoring," which is incorporated herein by reference in its entirety.

The substrate 40 is defined by a top surface 44, which is further defined by a fluid flow path 64. The fluid flow path 64 includes a plurality of discrete areas or zones in spaced relation to one another including a sample addition zone 48, a reagent zone 52, a plurality of detection zones 56 located in a detection channel 55 (for clarity, only one detection zone 56 is shown) and a receiving or wicking zone 60. According to this design, each of the above-noted zones are fluidly interconnected with one another in linear fashion along at least one defined fluid flow path 64 and in which a plurality of microposts 7, FIG. 1, are disposed within at least one of the zones and/or the flow channel, the microposts 7 extending upwardly from either the lower surface of the fluid flow path 64 or the discrete zones defined on the assay device 20.

The microposts 7 are preferably dimensioned to induce lateral capillary flow, wherein the microposts 7 preferably include a height, diameter and/or center to center spacing to induce fluidic flow along the at least one fluid flow path. In one version thereof, the microposts 7 can be sufficiently dimensioned so as to spontaneously induce capillary flow as a so-called "open" structure without the need for additional structure (i.e., side walls, cover or lid) or the application of any externally applied forces. According to this specific design, a defined fluid flow path 64 is created, extending from the sample addition zone 48 to the wicking zone 60. The illustrated fluid flow path 64 extends substantially in a straight-line fashion between the sample addition zone 48 and the wicking zone 60. In other configurations, the fluid flow path 64 can include one or more lateral bends or turns.

As noted and in various embodiments, the defined fluid flow path 64 is at least partially open, or entirely open. As noted above and by "open" what is meant is that there is no lid or cover which is maintained at a distance that would contribute to capillary flow. Thus a lid, if present as physical protection for the flow path and the device, is not required to contribute to the capillary flow in the flow path. According to this specific design, a hydrophilic foil layer 70 can be directly applied to the top of the microposts 7 in the wicking zone 60 in order to increase fluid flow in the device and in which a plurality of vents 72 can be defined in the foil layer. In various examples, a flow promoter 57 is arranged in the fluid flow path 64 bridging the edge of the hydrophilic foil layer 70 to promote flow under the hydrophilic foil layer 70 placed over the wicking zone 60.

Various examples of flow promoters, mixers, flow restrictors, and other structures useful for controlling flow in the fluid flow path 64 are described in U.S. Patent Application Ser. No. 62/035,083, filed Aug. 8, 2014, the disclosure of which is incorporated herein by reference in its entirety. That application describes examples of size and shape characteristics of sample addition zones 48 according to various aspects, features in the conjugate zone to effect more efficient dissolution according to various aspects, a curved portion of the fluid flow path 64 configured to mix fluid passing through the fluid flow path 64 according to various aspects, and features in the wicking zone 60 including flow promoters similar to the flow promoter 57 according to various aspects.

An open lateral flow path is described including the defined microposts 7, for example, in the following published applications: WO 2003/103835, WO 2005/089082; WO 2005/118139; WO 2006/137785; and WO 2007/149042, all of which are incorporated by reference in their entireties. The extending microposts 7 have a height (H), diameter (D) and a distance or distances between the microposts 7 such that lateral capillary flow of an applied fluid, such as plasma, preferably human plasma, in the zone having the microposts 7 is achieved. These relationships are discussed in U.S. Pat. No. 8,821,812, which is incorporated by reference in its entirety.

In addition to optimizing the above-mentioned height, diameter and a distance or distances, the above-noted microposts 7 may be given a desired chemical, biological or physical functionality, e.g. by modifying the surface of the microposts 7 for purposes, for example, of the reagent zone(s) and detection zone(s) 56 of the assay device 20. In one embodiment, the microposts 7 have a height in the interval of about 15 to about 150 µm, preferably about 30 to about 100 µm, a diameter of about 10 to about 160 µm, preferably 40 to about 100 µm, and a gap or gaps between the microposts 7 of about 3 to about 200 µm, preferably 5 to 50 µm or 10 to about 50 µm from each other. The fluid flow path 64 between the sample addition zone 48 and the wicking zone 60 may have a length of about 5 to about 500 mm, preferably about 10 to about 100 mm, and a width of about 0.3 to about 10 mm, preferably about 0.3 to about 3 mm, preferably about 0.5 to 1.5 mm. The microposts 7, according to this device design, are substantially cylindrical in terms of their configuration and cross section. However, their specific design of the microposts 7 can also easily be varied to those of different shapes (e.g., rhombic, hexagonal, etc) and sizes to augment flow, as well as to filter materials.

Still referring to FIG. 2, the sample addition zone 48 can receive a liquid sample from a liquid dispenser, such as a pipette or other suitable device. The sample is typically deposited onto the top of the zone 48. In various embodiments, a filter material (not shown) is placed within the sample addition zone 48 to filter particulates from the sample or to filter blood cells from blood so that plasma can travel through the assay device 20. In these embodiments, the sample is typically deposited onto the filter material.

The sample then flows, e.g., via capillary action of the microposts, to the reagent zone 52, which can include reagent(s) useful in the reaction, e.g., binding partners such as antibodies or antigens for immunoassays, substrates for enzyme assays, probes for molecular diagnostic assays, or auxiliary materials such as materials that stabilize the integrated reagents, materials that suppress interfering reactions, and the like. Generally, one of the reagents useful in the reaction bears a detectable signal as discussed herein. In some cases, the reagents may react with the analyte directly or through a cascade of reactions to form a detectable signal such as a colored or fluorescent molecule. In one preferred embodiment, the reagent zone 52 includes conjugate material. The term "conjugate" means any moiety bearing both a detection element and a binding partner.

For purposes of this description, a detection element is an agent which is detectable with respect to its physical distribution and/or the intensity of the signal it delivers, such as but not limited to luminescent molecules (e.g., fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element also referred to as a label is preferably chosen from chromophores, fluorophores, radioactive labels and enzymes. Suitable labels are available from commercial suppliers, providing a wide range of dyes for the labeling of antibodies, proteins and nucleic acids. There are, for example, fluorophores spanning practically the entire visible and infrared spectrum. Suitable fluorescent or phosphorescent labels include for instance, but are not limited to, fluoroceins, Cy3, Cy5 and the like. Suitable chemiluminescent labels include but are not limited to luminol, cyalume and the like.

Similarly, radioactive labels are commercially available, or detection elements can be synthesized so that they incorporate a radioactive label. Suitable radioactive labels include but are not limited to radioactive iodine and phosphorus; e.g., $^{125}$I and $^{32}$P.

Suitable enzymatic labels include but are not limited to horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or an amount of an analyte. For example, in a "sandwich" assay, the binding partner in the conjugate can form a complex including the analyte and the conjugate and that complex can further bind to another binding partner, also called a capture element, integrated into the detection zone 56. In a competitive immunoassay, the analyte will interfere with binding of the binding partner in the conjugate to another binding partner, also called a capture element, integrated into the detection zone 56. Example binding partners included in conjugates include antibodies, antigens, analyte or analyte-mimics, protein, etc.

As the sample interacts with the reagent in the reagent zone 52, the detection material begins to dissolve in which a resultant detectable signal is contained within the fluid flow, which is subsequently carried into the adjacent detection zone 56.

Still referring to FIG. 2, the detection zone 56 is where any detectable signal can be read. In a preferred embodiment and attached to the microposts 7 in the detection zone 56 are capture elements. The capture elements can hold binding partners for the conjugate or complexes containing the conjugate, as described above. For example, if the analyte is a specific protein, the conjugate may be an antibody that will specifically bind that protein to a detection element such as fluorescence probe. The capture element could then be another antibody that also specifically binds to that protein. In another example, if the marker or analyte is DNA, the capture molecule can be, but is not limited to, synthetic oligonucleotides, analogues, thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. The detection zone 56 can include multiple detection zones. The multiple detection zones can be used for assays that include one or more markers. In the event of multiple detection zones, the capture elements can include multiple capture elements, such as first and second capture elements. The conjugate can be pre-deposited on the assay device 20, such as by coating in the reagent zone 52. Similarly, the capture elements can be pre-deposited on the assay device on the detection zone 56. Preferably, both the detection and capture elements are pre-deposited on the assay device, or on the reagent zone 52 and detection zone 56, respectively.

Downstream from the detection zone 56 and along the fluid flow path 64 is the wicking zone 60. The wicking zone 60 is an area of the assay device 20 with the capacity of receiving liquid sample and any other material in the flow path, e.g. unbound reagents, wash fluids, etc. The wicking zone 60 provides a capillary pressure to continue moving the liquid sample through and out the intermediate detection zones 56 of the assay device 20. The wicking zone 60 and other zones of the herein described device 20 can include a porous material such as nitrocellulose, or alternatively is a non-porous structure defined by microposts 7, as previously described. The wicking zone 60 can further include non-capillary fluid driving means, such as an evaporative heater or a pump. Further details of wicking zones as used in lateral-flow assay devices according to the present invention are found in U.S. Pat. No. 8,025,854 and U.S. Patent Application Publication No. 2006/0239859 A1, both of which are incorporated herein by reference in their entireties.

Tests (assays) are typically completed when the last of the conjugate material has moved into the wicking zone 60 of the lateral-flow assay device 20. At this stage, a detection instrument, such as a fluorimeter or similar device, is used to scan the detection zone 56, the detection instrument being, e.g., incorporated within a portable (hand-held or bench top) testing apparatus. The detection instrument that can be used to perform the various methods and techniques described herein can assume a varied number of forms. For example, a mainframe clinical analyzer can be used to retain a plurality of lateral-flow assay devices as described in copending U.S. Patent Application Publication No. 2013/0330713 A1, the entire contents of which are herein incorporated by reference. In a clinical analyzer at least one detection instrument, such as a fluorimeter, can be provided, for example, in relation to an incubator assembly as a monitoring station in which results can be transmitted to a contained processor.

In various examples, the instrument can include a scanning apparatus that is capable of detecting fluorescence or fluorescent signals. Alternatively, an imaging apparatus and image analysis can also be used to determine, for example, the presence and position of at least one fluorescent fluid front of an assay device. According to yet another alternative version, infrared (IR) sensors could also be utilized to track the position of fluid position in the lateral-flow assay device. For instance, an IR sensor could be used to sense the ~1200 nanometer peak that is typically associated with water in the fluid sample to verify that sample had indeed touched off onto the substrate of the assay device. It should be readily apparent that other suitable approaches and apparatus capable of performing these techniques could be utilized herein.

The microposts 7, FIG. 1, are preferably integrally molded into the substrate 40 from an optical plastic material such as ZEONOR®, such through an injection molding or embossing process. The width of the detection channel 55 in the fluid flow path 64 is typically on the order of about 0.5 mm to about 4 mm, and preferably on the order of about 2 mm. Other portions of the fluid flow path 64 according to various examples can have widths of less than about 0.5 mm, or on the order of about 0.5 mm to about 4 mm, or greater than about 4 mm. Widths of about 1 mm can also be used for the detection channel 55, provided sufficient signal for a suitable detection instrument, such as a fluorimeter, can be read even if the reagent plume does not cover the entire width of the detection zone 56.

Components of the lateral-flow assay devices (i.e., a physical structure of the device whether or not a discrete piece from other parts of the device) described herein can be prepared from copolymers, blends, laminates, metalized foils, metalized films or metals. Alternatively, device components can be prepared from copolymers, blends, laminates, metalized foils, metalized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Alternatively, components of the device can be made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the lateral-flow assay devices are injection molded from a cyclic olefin polymer (COP), such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

Still referring to FIG. 2, the defined fluid flow path 64 of the lateral-flow assay devices described herein, including device 20, can include open or closed paths, grooves, and capillaries. In various embodiments, the fluid flow path 64 comprises a lateral flow path of adjacent microposts 7, FIG. 1, having a size, shape and mutual spacing such that capillary flow is sustained through the flow path. In one embodiment, the flow path is in a channel within the substrate 40 having a bottom surface and side walls. In this embodiment, the microposts 7 protrude from the bottom surface of the flow channel. The side walls may or may not contribute to the capillary action of the liquid. If the sidewalls do not contribute to the capillary action of the liquid, then a gap can be provided between the outermost microposts 7 and the sidewalls to keep the liquid contained in the flow path defined by the microposts 7. Preferably, the reagent that is used in the reagent zone 52 and the capture members or detection agent used in the detection zone 56 is bound directly to the exterior surface of the microposts 7 used in the herein described assay device 20.

Figure 3:
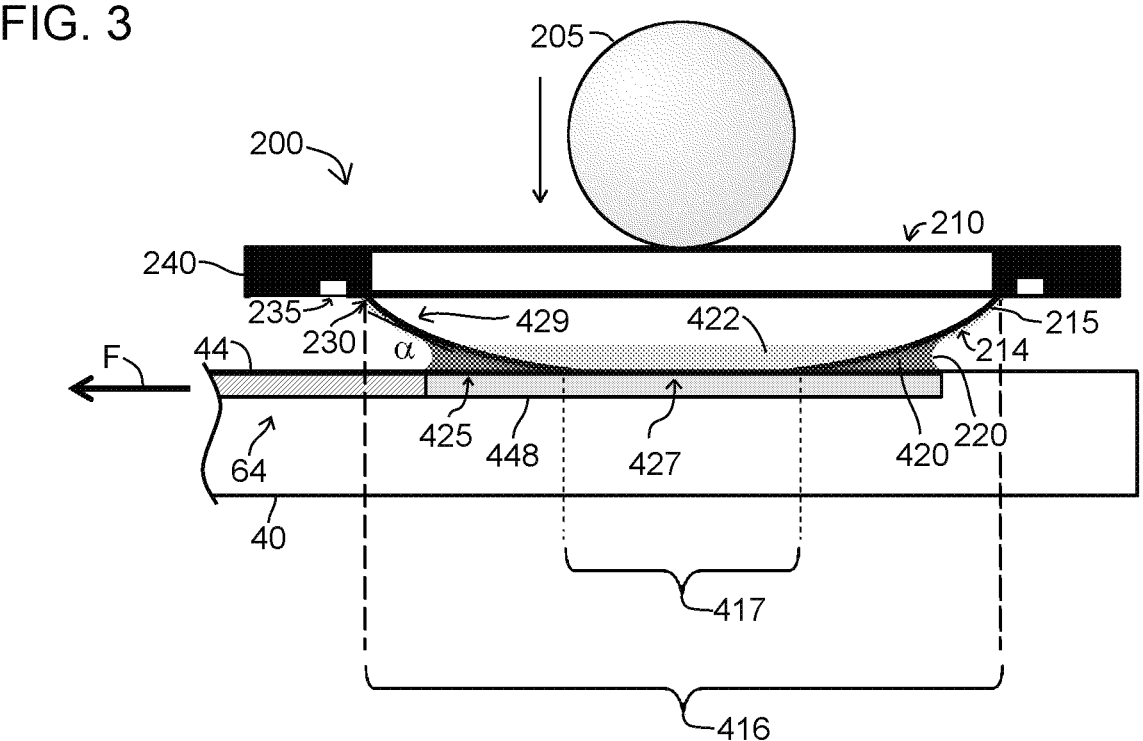
FIG. 3 illustrates a side elevational view of a lateral-flow assay device made in accordance with a first exemplary geometric relationship.

FIG. 3 is a side view of a portion of a lateral-flow assay device 400 for a sample made in accordance with a first exemplary geometric relationship in accordance with various embodiments. Similar parts are herein labeled with the same reference numerals for the sake of clarity. Whole blood, including plasma and red blood cells, is used in this discussion as a non-limiting example of a fluidic sample 205. The assay device 400 is herein defined by a planar substrate 40 having a sample addition zone 448 as part of at least one defined or created fluid flow path 64 through which a filtrate 420 flows under capillary action away from the sample addition zone 448 (e.g., in direction F). A cover or lid 240 is arranged over the substrate 40 and includes an aperture 210 defining a metering port configured to receive the sample 205.

A filter 215, e.g., having a substantially concave shape, is supported peripherally within the aperture 210 of the cover 240 and configured to permit at least a portion of the sample 205 to pass through the filter 215 as the filtrate 420. The filter 215 can be supported around the entire perimeter thereof by the cover 240, or the filter 215 can have some portions of the perimeter thereof supported by the cover 240 and other portions not supported. In an example of the latter configuration, the filter 215 can be supported at three, four, or another number of attachment regions (not shown) spaced around the aperture 210 in the cover 240. The portion of the sample 205 that does not pass through the filter 215 is referred to herein as the residue 422. The supported filter 215 includes at least one contact portion 427 in direct contact with the substrate 40 to create a contact area 417 that at least partly overlaps the sample addition zone 448. The filter 215 also includes an adjacent portion 429 that extends from the at least one contact portion 427 to the supported edge 230 (periphery) of the filter 215 to define with the substrate 40 a peripheral reservoir 425 that is capable of supporting or otherwise retaining a volumetric quantity of filtrate 420. For the purposes described herein, the filter 215 can be, e.g., substantially circular, elliptical, square, rectangular, or otherwise polygonal in lateral extent.

A flat surface contact between the filter 215 and the sample addition zone 48 would not produce reliable flow due to much larger flow resistance inside the filter 215 in a lateral flow. Filtration would therefore be less efficient due to much slower flow in the micropost matrix in a sample addition zone 448 beneath the flat filter 215. Therefore, a concave filter geometry such as that illustrated is preferred.

When the fluid sample 205 is dispensed onto the filter 215 in the sample addition zone 448 of the device, the filtrate 420 beneath the filter 215 contacts two surfaces, namely, the bottom of the filter 215 and the top surface 44 of the substrate 40. The surface 44 is at least partly hydrophilic, as is at least one surface 214 of the filter 215 facing the surface 44. As a result, the filtrate 420 wets the surface 44 and the surface 214, forming a meniscus 220. The meniscus 220, the surface 214, and the surface 44 bound the peripheral reservoir 425.

The peripheral reservoir 425 is configured to retain the filtrate 420 by means of capillary pressure developed between the substrate 40 and the extending portion 429 of the filter 215. In various embodiments, there is substantially no difference in ambient pressure (e.g., atmospheric pressure) across the filter 215, and the capillary pressure provides substantially all of the force driving filtrate 420 through the filter 215. In an example, the peripheral reservoir 425 is defined by a volume based on an acute angle α (e.g., about 10°) that is formed between the substrate 40 and the extending portion 429 of the filter 215. The volume is also based on the meniscus 220. The reservoir 425 serves to supply plasma or other filtrate 420 during a filtration process and after filtration is complete for the whole blood or other fluid sample 205. The sample addition zone 448 is configured to provide a capillary pressure drawing the filtrate 420 from the reservoir 425 to the sample addition zone 448, as discussed below. For example, the filter 215 and the sample addition zone 448 can be configured to provide a capillary pressure drawing the filtrate 420 through the filter 215, and providing the filtrate 420 from the reservoir 425 to supply consistent flow through the sample addition zone 448 of the lateral-flow assay device 400. The drawn filtrate 420 can then flow downstream from the sample addition zone 448 along the fluid flow path 64.

In various embodiments, the device 400 includes at least one reagent zone 52, FIG. 2, disposed along the fluid flow path 64 downstream of the sample addition zone 448. The reagent zone retains at least one detection material, as discussed above. In various embodiments, the device 400 further includes a detection zone 56, FIG. 2, disposed along the fluid flow path 64 downstream of the sample addition zone 448. The detection zone 56 includes a detection material responsive to an analyte to produce a detectable signal. Detection of signals is discussed above and is discussed below with reference to FIG. 11.

As noted above, the sample addition area 448 draws the filtrate 420 from the reservoir 425 by capillary pressure. In various embodiments, the substrate 40 includes a plurality of microposts 7, FIG. 1, extending upwardly from the surface 44 toward the cover 240 in the sample addition zone 448. The microposts 7 are defined by heights, diameters and reciprocal spacing between the microposts 7 that spontaneously induce lateral capillary flow upon the application of filtrate 420 thereto.

After the sample 205 is applied to the filter 215 the liquid filtrate 420 that flows through the filter 215 wets the surface 44 and the microposts 7, FIG. 1, in the sample addition zone 448 beneath the filter 215. A capillary pressure is thus generated between the wetted microposts 7 along the fluid flow path 64 of the device 400. As the filtrate 420 reaches the space between the filter 215 and the top of the microposts 7 in the sample addition zone 448 of the device 400, one or more menisci (not shown and, for the avoidance of doubt, not the illustrated meniscus 220) are formed in the tiny gaps formed by the filter 215 and the device surface 44 due to capillary effects. Filtrate 420 also flows downstream along the matrix of microposts 7 as driven by the capillary pressure created between the microposts 7. A more detailed description of the microposts 7 and their design to create spontaneous lateral capillary flow is provided in U.S. Pat. No. 8,025,854 to Ohman et al., issued Sep. 27, 2011, the entire contents being incorporated by reference.

In one version, capillary pressure developed by the flow control elements (e.g., the microposts 7) on the substrate 40 is sufficiently large to overcome the capillary pressure maintaining the peripheral meniscus 220. This causes the volumetric fluid to be drawn from the peripheral reservoir 425 wherein the flow rate of the assay device (out of the peripheral reservoir 425) is slower than that of the filtrate flow rate (into the peripheral reservoir 425). In an example, substantially all the filtrate 420 passes from the sample 205 into the reservoir 425 in about one minute, but at least some of the filtrate 420 is retained in the reservoir 425 for about ten minutes during the conduction of the assay.

Dynamically and if the inflow rate (i.e., filtration rate at which filtrate 420 passes through the filter 215) is higher than the outflow rate (i.e., the channel flow rate at which the filtrate 420 passes from the peripheral reservoir 425 into the fluid flow path 64 as provided by the micropost matrix), the perimeter of the meniscus 220 and the volume of reservoir 425 will increase. If the meniscus 220 grows too large, however, the meniscus 220 may engage the edge 230 of the filter 215 where fluid can be trapped without participating in the assay reaction. The creation of trapped fluid can lead to a shortage of sample flowing to the end of the wicking zone 5, FIG. 1, which is undesirable especially when using smaller sample volumes (e.g., microsamples of 50 μL or less). In cases in which the meniscus 220 reaches the supported peripheral edge 230 of the filter 215 and the underside of the cover 240, which may include various obstructions, such as a welding groove 235, sample fluid can become trapped. This trapping is referred to as "latching" of the meniscus or fluid. Latched filtrate 420 can fill the welding groove 235 or otherwise latch onto the underside of the cover 240 (in general, the side facing the substrate 40). As a result, less filtrate 420 (e.g., plasma) will be available to flow downstream along the fluid flow path 64 toward the reagent zone 52, detection zone 56, and wicking zone(s) 60 of the assay device 400. Moreover, the preceding effect can also deleteriously stop or impede flow within the fluid flow path 64, or cause flow to occur very slowly due to lack of fluid sample in the meniscus 220.

For whole blood filtration, the meniscus 220 between the filter 215 and the assay device substrate 40 grows initially when the pores of the filter 215 are relatively open and the hematocrit (HCT) level of the sample 205 is still close to a normal range. In the later phases of filtration, most of the filter 215 pores become clogged by the red blood cells, and blood HCT level in the residue 422 increases as a result of losing plasma to the other side of the filter 215. As a result, inflow into the reservoir 425 from filtration becomes slower than outflow from the reservoir 425 toward the wicking zone 60 of the device 400, and the meniscus 220 and reservoir 425 volume shrink.

The peripheral reservoir 425, with the meniscus 220 as a movable sidewall, permits fast filtration and much slower, but desirable channel flow. In an example, a channel flow rate of about 0.5 to 2.0 μL/minute is desirable for about a 10-15 minute total assay time and enough reaction time to generate a sufficient signal for acceptable assay sensitivity.

As noted, the volume in the reservoir 425 of the fluid from sample 205 is determined by the size and shape of the contact area 417, the size and shape of the filter 215, and the angle α formed between the filter 215 and the top surface 44 of the substrate 40.

Various prior devices use reduced filter size to reduce plasma waste within the filter 215. However, this can increase the risk of filtered plasma being trapped at the filter 215 if the meniscus 220 beneath the filter 215 reaches the peripheral edge 230 of the filter 215 and becomes latched thereto. Various other devices use very small volumes of sample, which can increase the likelihood of errors in testing since less fluid is involved in the assay.

According to various embodiments and in order to control the size of the meniscus 220 (e.g., prevent the meniscus 220 from reaching the supported edge 230 of the filter 215) and reduce plasma waste without the disadvantage of latching, two different geometric relationships between the contact area, sample zone size and filter size have been developed. These relationships are herein discussed in greater detail and with reference to FIGS. 3 and 4.

Still referring to FIG. 3 and according to the first geometric relationship, the assay device 400 is configured such that the contact area 417 of the assay device 400 is made smaller than the sample addition zone 448. Specifically, the sample addition zone 448 extends laterally beyond the contact area 417. In addition and according to this device design, the sample addition zone 448 is made smaller than the filter area 416. In this exemplary device design, the edge of the sample addition zone 448 serves as a barrier to pin the meniscus 220 and prevent the meniscus 220 from spreading. That is, the surface energy of a top surface 44 of the substrate 40 is different outside the sample addition zone 448 than inside the sample addition zone 448, and that difference tends to resist flow of the filtrate 420 beyond the bounds of the sample addition zone 448 at the top surface 44 of the substrate 40. By way of example and for a filter area 416 having a diameter of about 7 mm, the diameter of the contact area 417 can be about 2.5 mm and the diameter of the sample addition zone 448 can be about 5 mm.

In various embodiments, the substrate 40 can have a non-planar top surface 44 proximate to the contact area 417. For example, both the filter 215 and the substrate 40 can be curved in at least part of the filter area 416, or the filter 215 can be substantially flat and only the substrate 40 can be curved. As long as angle α>0° is present and the sample addition zone 448 and filter 215 are configured with the functional structures defined herein, reservoir 425 will be defined between filter 215 and surface 44. The device 400 and the size of sample 205 can be co-optimized so that the reservoir 425 has enough space to hold the filtrate 420 and prevent latching of the meniscus 220, and provides enough driving force that the filtrate 420 moves from the fluidic sample 205 to the fluid flow path 64 in a desired amount of time.

Figure 4:
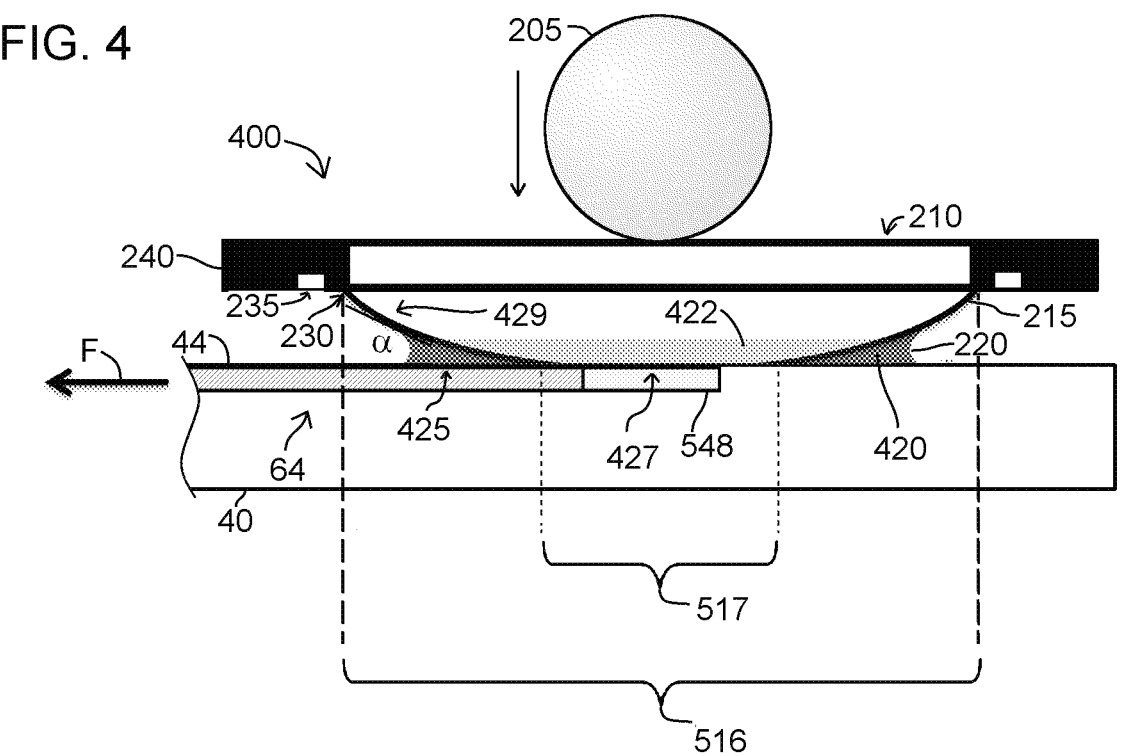
FIG. 4 illustrates a side elevational view of a lateral-flow assay device made in accordance with a second exemplary geometric relationship.

FIG. 4 is a side view of a lateral-flow assay device 400 made in accordance with a second exemplary geometric relationship and in accordance with various embodiments. According to this geometric relationship, the assay device is configured such that the area of sample addition zone 548 is defined to be smaller than that of the contact area 517, with the latter area 517 also being less than the filter area 516. Specifically and as shown, the contact area 517 extends laterally beyond the sample addition zone 548.

In this design and according to FIG. 4, less fluid is present in the sample addition zone 548 at any given time than in the prior designs using larger sample addition zones 548 and can reduce the volume of the filtrate 420 that ultimately cannot be extracted from the sample zone 547. The sample addition zone 548 is connected with the fluid flow path 64 of the assay device 400.

By way of example and for a filter area 516 having a diameter of about 7 mm, the contact area 517 can have a diameter of about 2.5 mm and the sample addition zone 548 can have a diameter of about 2 mm. The much smaller sample addition zone 548 results in much less fluid waste since filtrate 420 filling the space between the microposts 7, FIG. 1, in the sample addition zone 548 will remain inside the sample addition zone 548 and will not flow downstream. By making the sample addition zone 548 smaller, less fluid will be wasted in the sample addition zone 548.

An inventive test strip similar to that illustrated in FIG. 4 can be constructed with a substantially concave-shaped filter 215. An exemplary inventive test strip was constructed in which the area of the sample addition zone 548 was smaller than the contact area 517, which was smaller than the filter area 516. The sample addition zone 548 had a volume about 1.2 μL less than a comparative design, saving about 25% of the fluid for a wicking zone 60 having a volume of 4.5 μL. The supported filter 215 was coated with 1.5% SILWET surfactant and 5% glycine and was dried for 1 hr at 60° C. and 5% RH. A 50%-HCT whole blood sample was spotted to the filter 215 at different volumes and flow times were measured. Longer flow times suggest a shortage of plasma due to reduced plasma extraction from the sample addition zone 548. This is because flow slows as the fluid supply is reduced. Table 1 shows experimental results of the time for the fluid to reach the start or end of the wicking zone 60 ("WZ") for two volumes of sample 205 (25 μL and 30 μL), and for a comparative device and an inventive device.

TABLE 1

| Sample volume | Device | Average Time to Start WZ | | | Average Time to End WZ | | |
|---|---|---|---|---|---|---|---|
| | | Mean | SD | CV | Mean | SD | CV |
| 25 μL | Comparative | 0:01:47 | 0:00:10 | 9.27 | 0:12:33 | 0:01:00 | 7.97 |
| 30 μL | Comparative | 0:01:42 | 0:00:02 | 2.12 | 0:08:57 | 0:00:24 | 4.50 |
| 25 μL | Inventive | 0:01:20 | 0:00:05 | 6.56 | 0:10:33 | 0:00:32 | 5.11 |
| 30 μL | Inventive | 0:01:19 | 0:00:09 | 10.80 | 0:08:13 | 0:00:26 | 5.33 |

As Table 1 shows, with the lower sample volume at 25 μL, the flow time for the inventive device to reach the end of the wicking zone 60 is about 2 minutes faster than the comparative device, showing that the inventive device is wasting less plasma (filtrate 420) in the sample addition zone 548 since flow slows as fluid supply diminishes.

For both 25 μL and 30 μL blood samples, fluid reaches the wicking zone 60 faster in the inventive design than in the comparative design, indicating that less sample 205 is wasted to fill the pillar space under the filter 215 in the inventive design than in the comparative design.

Increasing the angle α (the angle subtended between the non contacting portion 429 of the filter 215 and the surface 44 of the device substrate 40) in either of the devices 200, 400 according to FIGS. 3 and 4, reduces or controls filtration due to reduced capillary pressure between the filter 215 and the device 400 (with all other conditions remaining the same). The increase in angle α also increases the volume of the peripheral reservoir 425, i.e., the volume available to hold filtrate 420 before the meniscus 220 reaches the supported edge 230 of the filter 215 and the underside of the cover 240 of the device.

A smaller angle α between the filter 215 and the top surface 44 of the substrate 40 of the herein described lateral assay device 400 will create a larger capillary pressure to drive filtration flow into the reservoir 425 and therefore flow out of the sample 205 should be comparatively faster (all other conditions remaining the same). However, angles α that are too small, e.g., less than about 2 degrees, can leave little space to hold the filtrate 420. Such a configuration can lead to the filtrate 420 reaching the supported edge 230 of the filter 215 and the underside of the cover, resulting in trapped fluid that will not participate in flow to the reagent zone(s) 52 or the detection zone(s) 56 of the herein described device 400.

If the angle α becomes zero, the only driving force for filtration becomes the spacing and dimensions of the microposts 7, FIG. 1, and their matrix, which can only generate very slow flow and very slow filtration. Flow stoppage is likely to occur as a result for several reasons, e.g., a gradual blockage of the filter 215 since fluid tends to flow in the front (downstream) edge of the filter 215, or a slower flow due to larger flow resistance in the micropost matrix under the filter 215. Accordingly, in various embodiments, α>0°.

Consequently, it is desirable to augment the angle α to increase filtration rate, while permitting a created peripheral reservoir 425 to retain a sufficient volume of filtrate 420 without latching. As a result of the foregoing, a variation of the prior geometric relationships/designs is shown in FIGS. 5A and 5B.

Figure 5A:
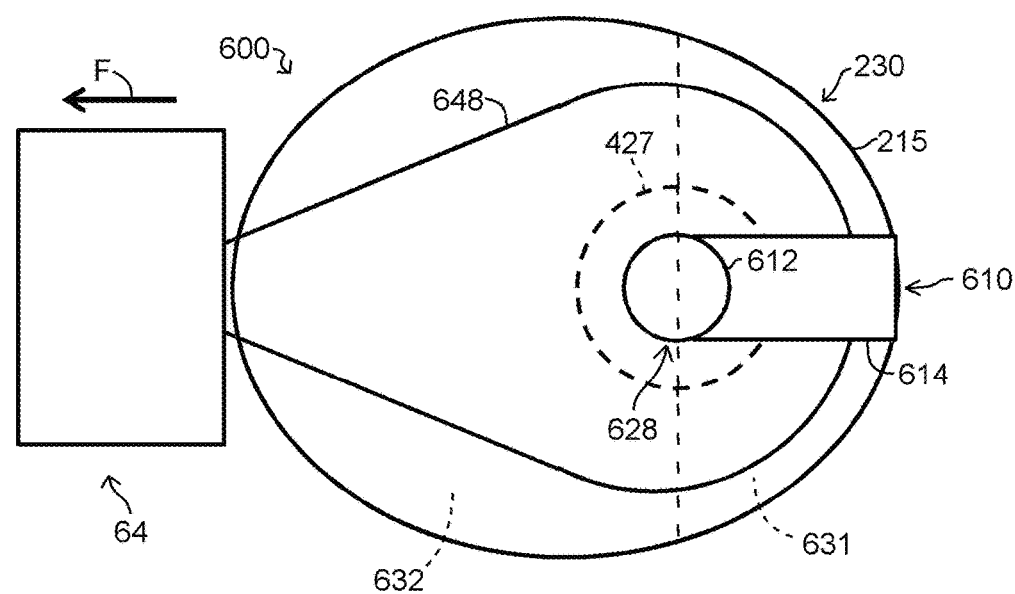
FIG. 5A illustrates a top plan view of a lateral-flow assay device made in accordance with a third exemplary geometric relationship.
Figure 5B:
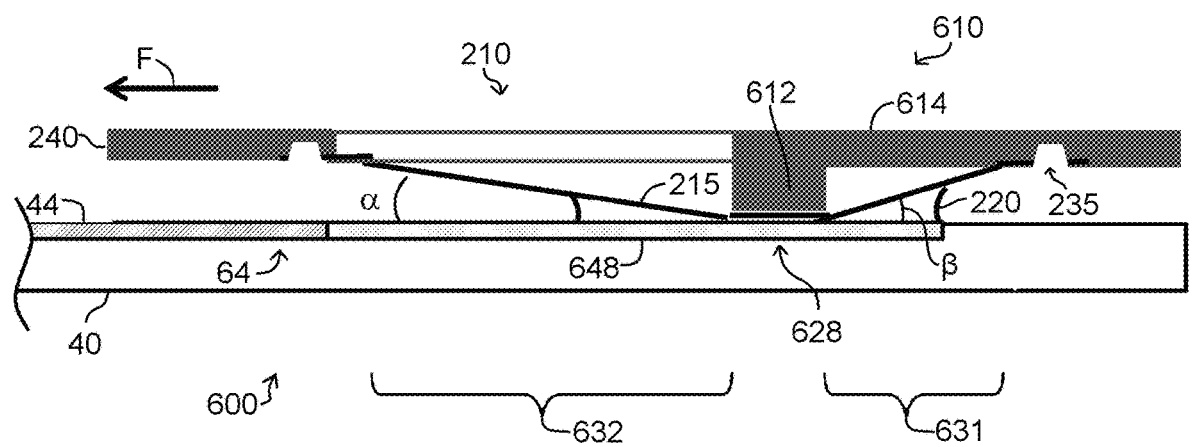
FIG. 5B illustrates a side view of the lateral-flow assay device of FIG. 5A.

FIG. 5A illustrates a top plan view, and FIG. 5B a side elevational cross-section, of a lateral-flow assay device 600 made in accordance with another exemplary design. According to this latter design, an engagement feature 610, e.g., at least one nub, can be provided that pushes against or engages at least one portion of the supported filter 215 acting toward the substrate 40 (i.e. downwardly) and wherein the nub or other feature can be centrally or eccentrically positioned relative to the filter 215. That is, the nub can be positioned at or relative to the center of the filter 215. As a result of this engagement feature 610, the angle α between the device substrate 40 and the filter 215 can be controlled so as to differ locally over one or several regions of the filter 215. The angles in the various regions can be selected by adjusting the location of the nub or other similar engagement feature 610 with respect to the filter 215. This latter design can permit more plasma (or other filtrate 420) to be stored in defined larger-angle regions while still maintaining high flow rates in defined smaller-angle regions, e.g., downstream portions, due to a smaller angle produced between the filter and the device substrate (i.e., larger capillary pressure).

A major advantage of engagement features 610, such as a nub, is that of better defining the filter 215 shape in the manufacturing process. For example and by using various nub heights and sizes, the filtration rate as controlled by the capillary pressure between the substrate surface 44 and the filter 215 (given the filter 215 and the sample 205) can be predefined. For example, a first nub extending normal to the cover 240 by a certain amount results in a certain angle α between the filter 215 and the surface 44 of the substrate 40. A second nub extending normal to the cover 240 by a larger amount than the first nub will result in a larger angle α. The larger angle α leads to smaller capillary pressure and larger volume to hold the filtrate 420 using the second nub compared to using the first nub, at the same wetting area in the lateral-flow assay device 600.

In various embodiments, the filter 215 can be defined by a substantially concave shape and an angle α extending from the contact portion 427 to an edge 230 of the filter 215, which can be coincident with or adjacent or attached to an edge of the defined cover aperture 210. The device 600 further comprises at least one feature that controls the angle. For example, the feature can include a projecting member 610, FIG. 5A, which can include a nub 710, FIG. 6. Further details of exemplary features are discussed below.

Referring to FIG. 5A, the device 600 includes one or more projecting member(s) 610 arranged to press or otherwise engage the at least one contact portion 427 of the filter 215 against the substrate 40. As shown, it is not required that the area of the projecting member 610 precisely overlap the area of the contact portion 427. In various embodiments, such as that shown, the at least one projecting member 610 eccentrically engages a portion 628 of the supported filter 215. In the example shown in FIG. 5A, the portion 628 of the filter that is engaged by the at least one projecting member 610 is depicted to the right of the center of the filter 215.

FIG. 5B is a side view in elevation showing details of an exemplary projecting member 610. The illustrated projecting member 610, or, in general, at least one of the projecting member(s) 610, includes a tip 612 in contact with the filter 215 and a cantilevered portion 614 supporting the tip 612 with respect to the cover 240. In this way, more of the aperture 210 is open, as compared to a cover 240 that directly supports the tip 612.

In various embodiments, at least one of the projecting member(s) 610 is arranged to define at least a first portion 631 and a second portion 632 of the filter 215. The first portion 631 of the filter 215 forms a larger angle β with the substrate 40 than that formed by the second portion 632 of the filter 215 (angle α). As noted above, this arrangement of two portions 631, 632 permits more fluid to be stored in the peripheral reservoir 425, FIG. 3, in the first portion 631 with the larger angle β, and maintains capillary pressure in the second portion 632 with the smaller angle α. In the example shown, the first portion 631 of the filter 215 is upstream of the second portion 632 of the filter 215 with respect to the fluid flow path 64 (direction F points downstream). In an example, angle β is about 5°, angle α is about 3°, and a corresponding angle between the surface 44 and the filter 215 into and out of the plane of the device of FIG. 5B (up and down in FIG. 5A) is about 2.5°.

The examples described above include a single fluid flow path 64 extending from the sample addition zone 648. However, multiple fluid flow paths 64 can be provided in relation the sample addition zone 648. For example, three fluid flow paths 64 (not shown) can be provided, each of the fluid flow paths being spaced evenly or unevenly around the perimeter of the sample addition zone 648 and extending therefrom. This arrangement can permit multiple assays to be performed using a single sample.

In addition and though each of the preceding embodiments are defined by a single sample addition zone 648, it will be understood that multiple spaced-apart sample addition zones 648 could be disposed over a substrate 40, each being at least partly in the contact zone 517, FIG. 4. Also or alternatively, multiple spaced-apart contact zones 517 can be provided, e.g., by using a projecting member 610 having multiple spaced-apart tips 612. For example, the sample addition zone 548 can be shaped like a dumbbell and two contact zones 517 can be arranged at the centers of the bulges at either end of the sample addition zone 548.

Moreover, the sample addition zone(s) 548 or contact zone(s) 517 can be any shape, including non-convex shapes or shapes with holes. In an example, the sample addition zone 548 forms a ring around the perimeter of the contact zone 517. The shape of the sample addition zone 548 and the contact area 517, and the angles (including angles α and β) can be selected to influence the direction and rate of flow of the filtrate 420. These shapes and angles can also be selected to control the shape of the peripheral reservoir 425, FIG. 3, as filtrate 420 flows in and out of the reservoir 425. For example, the peripheral reservoir 425 can assume a figure-8 shape, a donut shape, or other suitable shapes as the filtrate 420 flows in to the defined peripheral reservoir 425. The shape of the reservoir 425 can be selected based on mechanical characteristics, e.g., to permit the lateral-flow assay device to be produced in a long, narrow form factor while retaining the filtrate 420 in a long, narrow reservoir 425 to reduce the probability of latching.

The shape and location of the various engagement features such as the nub(s), as well as the specific number of nubs to be provided to the device, can easily be varied as shown according to exemplary versions which are herein depicted at FIGS. 6-10. Features of the substrates 40 are shown transparent for clarity of explanation. Each of these depicted examples use circular apertures 210 arranged over oblong sample addition zones 648, but it will be readily understood that other shapes can easily be substituted. For purposes of clarity, the filter is not shown in these examples, but would extend over a larger area than the cover aperture 210.

Figure 6:
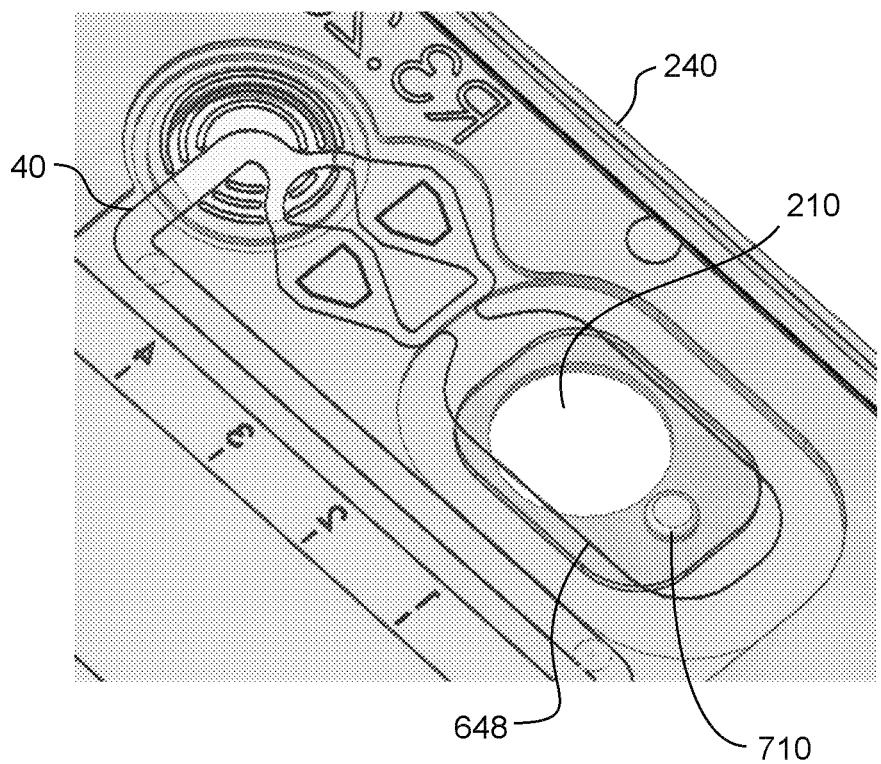
FIGS. 6-10 are bottom perspective views of lateral-flow assay devices made in accordance with other exemplary embodiments, each of the depicted devices being useful for purposes of the methods described herein.

By way of example, FIG. 6 shows a single substantially circular nub 710 which is arranged near the perimeter of the cover aperture 210.

Figure 7:
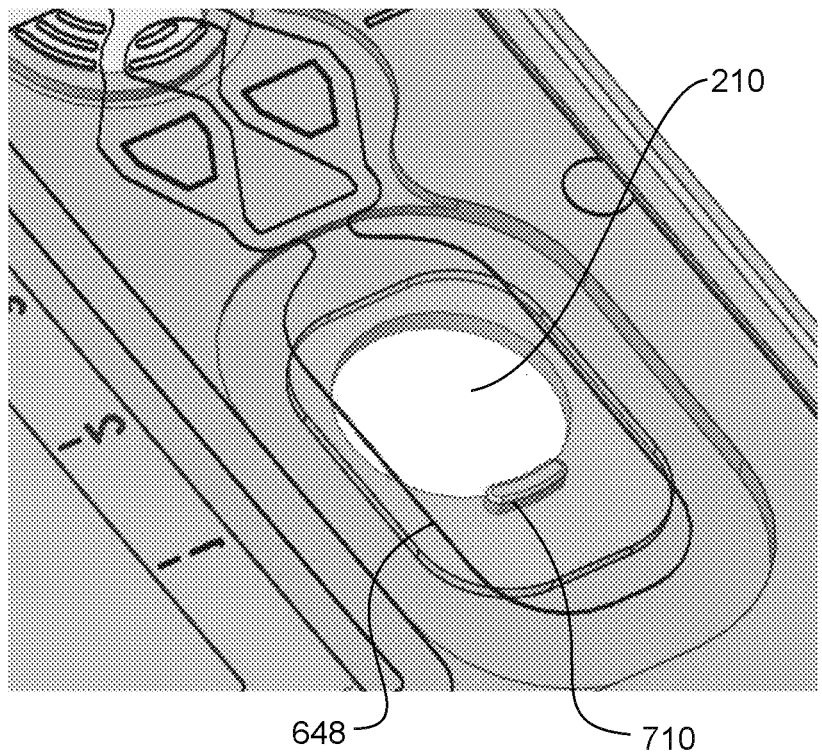

FIG. 7 shows another suitable example having a single, crescent-shaped nub 710. More particularly, the nub 710 according to this exemplary version is defined by a curved periphery configured to substantially follow a curved portion of the edge of the cover aperture 210.

Figure 8:
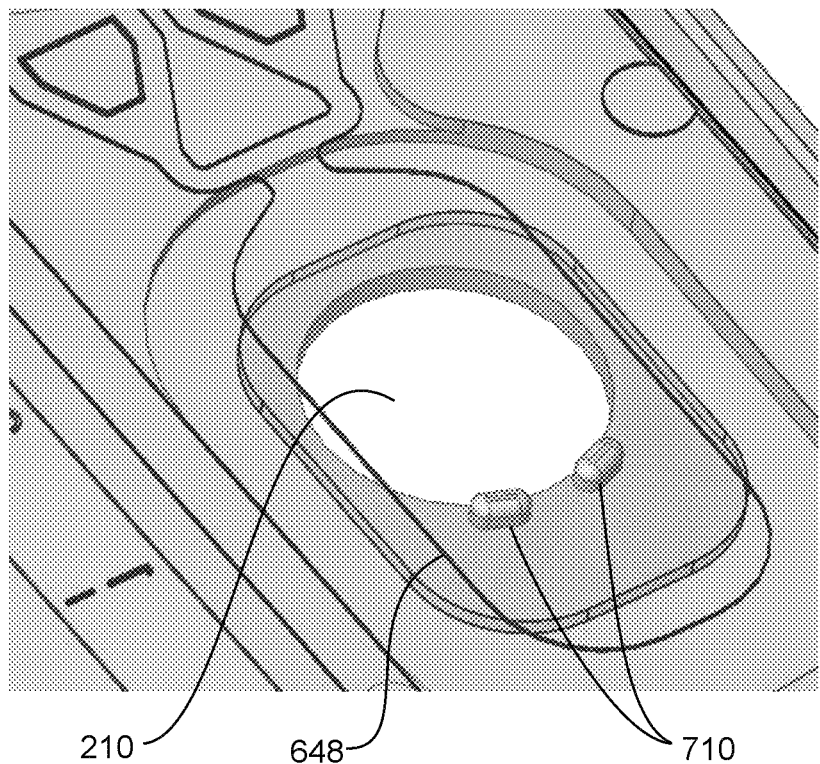

FIG. 8 shows another variation, by way of example, providing multiple engagement features. In this specific example, a pair of spaced partially curved nubs 710 are provided on one side of the cover aperture 210, each nub 710 having a curved periphery configured to substantially follow a portion of the edge of the cover aperture 210, with each nub 710 being spaced apart from the other.

Figure 9:
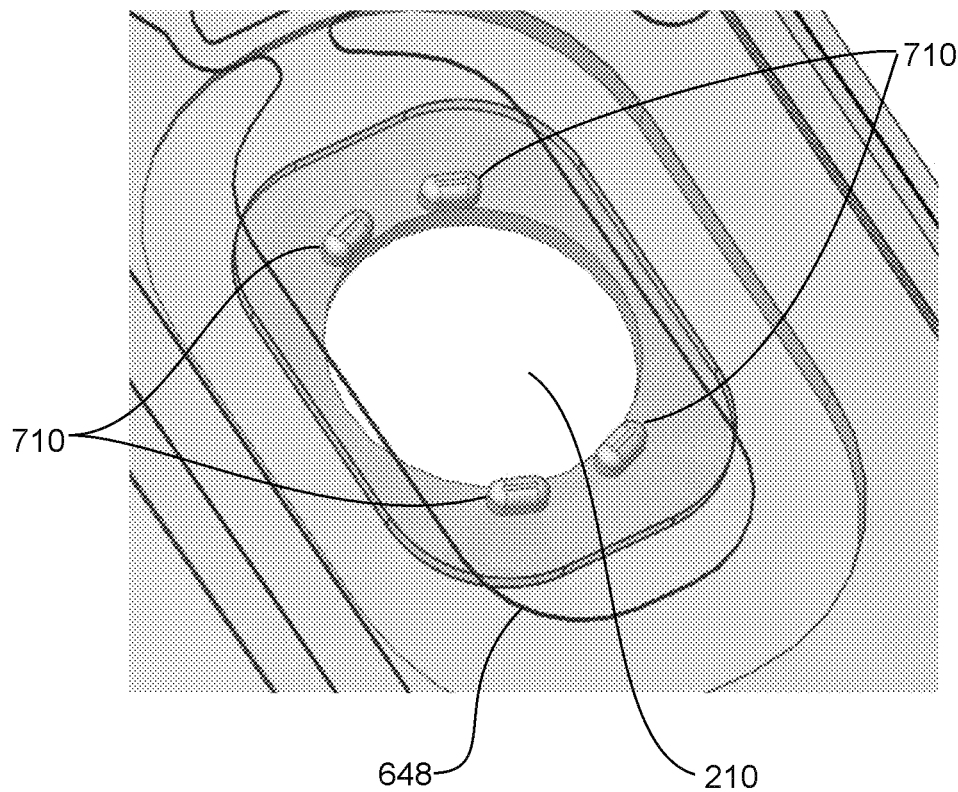

FIG. 9 shows another exemplary variation that includes a plurality of spaced-apart partially curved nubs 710. The nubs 710 according to this exemplary version are also curved to substantially follow a curved portion of the cover aperture 210, and are evenly spaced apart from each other. According to this specific version, two pairs of nubs 710 are provided in spaced relation with one another on opposing sides of the cover aperture 210. It will be readily apparent to those of sufficient skill in the field, however, that a nearly limitless myriad of variations and modifications are possible. For example, instead of or in addition to of one or more of the nubs 710 shown in FIGS. 6-9, engagement features 610 having cantilevered portions 614, FIG. 6, and supporting tips 612, FIG. 6, can be used. Such engagement features 610 can protrude into the cover aperture 610.

Figure 10:
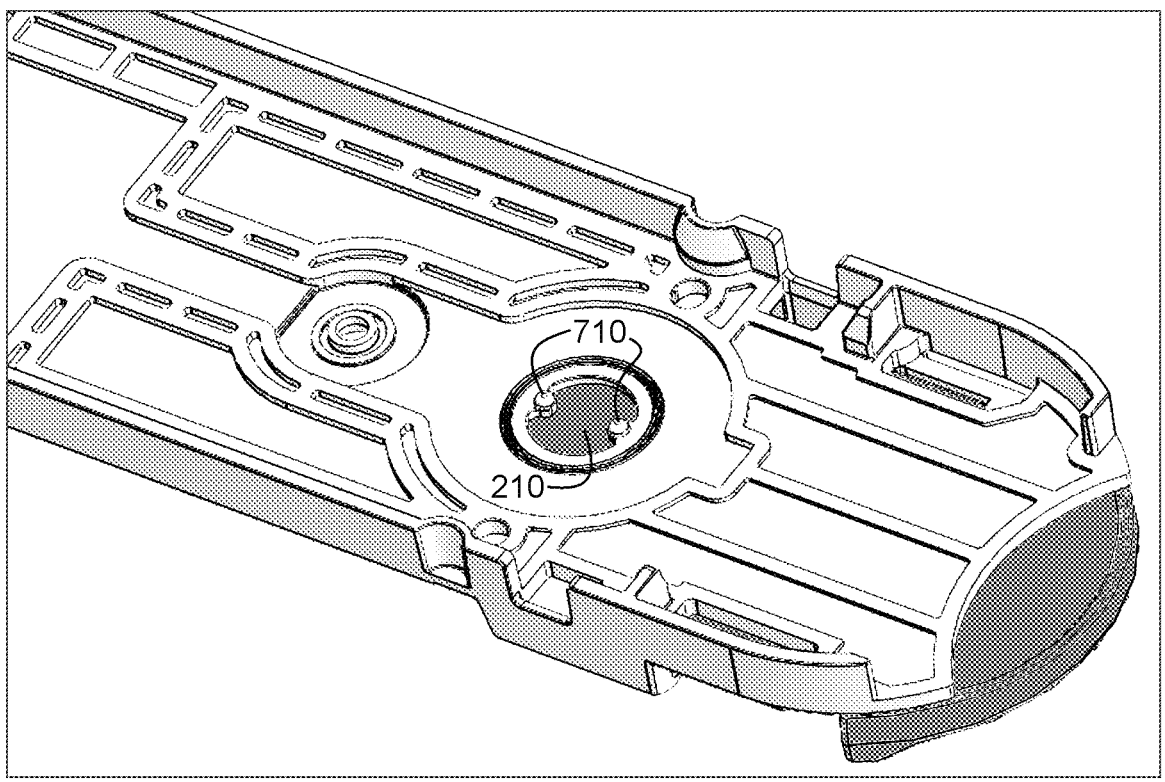

Finally, FIG. 10 shows another variation and more specifically the underside of a cover in which two substantially circular nubs 710 can be arranged opposite each other and extending into a portion of a cover aperture 210.

One exemplary flow controlling methodology is now herein described. For purposes of this method and in the description that follows, a lateral-flow assay device as previously described according to FIG. 3 is utilized, although other device configurations could be utilized, this embodiment intended to be exemplary of a more generic technique. The steps can be performed in any order except when otherwise specified, or when data from an earlier step is used in a later step.

Figure 11:
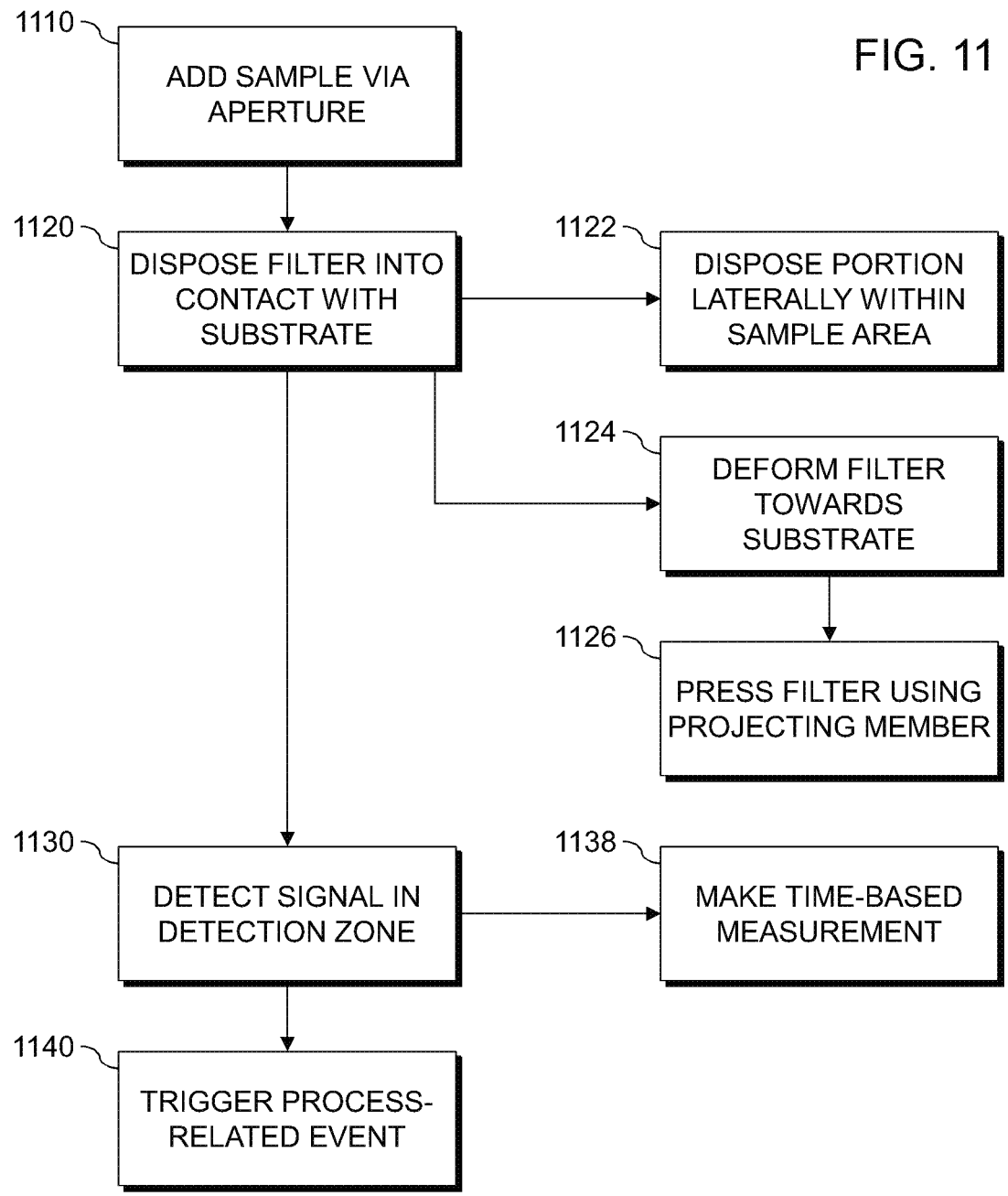
FIGS. 11-12 are flowcharts of exemplary methods for controlling filtration or flow characteristics in a lateral-flow assay device according to various embodiments.

FIG. 11 is a flowchart of a method for controlling filtration or flow characteristics in a lateral-flow assay device such as a device 200, FIG. 3, or device 400, FIG. 4. As previously described, the device 200 includes a cover 240 and a substrate 40. The cover 240 has an aperture 210 sized and configured to receive a fluidic sample 205, such as whole blood and peripherally supporting a filter 215. The substrate 40 of the device 200 has a sample addition zone 448 and a fluid flow path 64 through which a filtrate 420 flows under capillary action away from the sample addition zone 448. The substrate 40 can includes a plurality of microposts 7, FIG. 1, extending upwardly from a top surface 44 toward the cover 240 in the sample addition zone 448. The microposts can each have heights, diameters and reciprocal spacings between the microposts that induce lateral capillary flow upon the application of filtrate 420 thereto. In various embodiments of methods and devices described herein, the microposts can be spaced and sized to provide a selected flow rate out of a defined peripheral reservoir 425 that extends from a contact area of the filter with the substrate 40, the peripheral reservoir 425 being formed based on capillary action between a non-contacting portion 429 of the filter 215 and the top surface 44 of the substrate 40 directly beneath the cover aperture 210 to form a volume further defined based on an angle α between the underside of the filter 215 (e.g., the surface 214, FIG. 3), which is hydrophilic and the top surface 44 of the substrate 40, which is also preferably hydrophilic. In various embodiments, the method begins with step 1110.

In step 1110, a selected quantity of a sample is added via the aperture 210 to the device 200. The sample can be added using a pipette or other dispensing device. The dispensing device can be operated directly by a human, or can be automatically controlled, e.g., by a controller in an automated assay-testing system.

In step 1120, at least one portion 427 of the filter 215, e.g., a contact portion, is disposed into contact with the substrate 40 at least partly over the sample addition zone 448. As a result, the filtrate 420 passes through the filter 215 from the sample 205 at a first flow rate. The filtrate 420 is retained by capillary pressure in the peripheral reservoir 425 or other volume between the substrate 40 and an extending hydrophilic portion 429 of the filter 215 spaced apart from the substrate 40 and extending to an outer periphery (edge 230) of the supported filter 215.

Moreover, the filtrate 420 is drawn by capillary pressure from the volume (e.g., reservoir 425) into the sample addition zone 448 at a second flow rate slower than the first flow rate. As noted above, this permits filtrate 420 to be held in the reservoir 425 to even out the flow rate mismatch between the dispensing device and the lateral-flow assay device 200. Specifically, the quantity of the sample 205 is determined based on the first and second flow rates and on a limit of the volume (the reservoir 425). The limit of the volume is determined by at least one angle α subtended between the substrate 40 and the extending hydrophilic portion 429 of the filter 215. In an example, the quantity is chosen so that, at the peak of the fluid volume held in the reservoir 425, the meniscus 220 does not reach the welding groove 235. This permits using a higher percentage of the sample 205 than prior assay devices, so a smaller quantity of the sample 205 can be used than in prior systems. As a result, more tests can be performed less intrusively. Step 1120 can be followed by step 1130. In various embodiments, step 1120 includes steps 1122 or 1124.

In at least one embodiment of step 1120, the area of the filter 215 is made greater than that of the sample addition zone at the substrate 40. An example is shown in FIG. 3, in which the filter area 416 extends farther on each side than does the sample addition zone 448.

In step 1122, the disposing step further comprises disposing the at least one contact portion 427 laterally within the sample addition zone 448 at the substrate 40. For example, pre-formed dome-shaped filters 215 can be used. The device 400 can be assembled so that such a filter 215 is brought into contact with an appropriate area on the substrate 40. Pre-formed filters can be produced by heating filter material and pressing it in a mold, or by drying paper or other fibrous filter material in a mold.

In step 1124, at least a portion of the supported filter is deformed toward the substrate 40. In some embodiments using step 1124, for example, a material is used for the filter 215 that is at least partly compliant or deformable. The filter 215 is installed in the cover 240 in a flat configuration or another configuration that does not contact the top surface 44 of the substrate 40. The filter is then deformed toward the substrate 40 until it contacts the substrate 40 at least partly over the sample addition zone 448. The deformation can be, e.g., eccentrically deformation of the filter relative to a lateral center of the filter. FIGS. 5A and 5B show an example of eccentric (off-center) deformation.

Step 1124 can be performed, e.g., when the device 400 is manufactured. For example, the filter 215 can be deformed towards the substrate 40 using at least one projecting member of the cover 240 when the cover 240 is mounted to the substrate 40. Step 1124 can also or alternatively be performed when the device 400 is ready for use, e.g., before the sample 205 is added, while the sample 205 is being added, or after the sample 205 is added but before the sample 205 or the filtrate 420 begins to drip. In various embodiments, step 1124 includes step 1126.

In various embodiments, step 1124 includes deforming the filter to define at least a first portion 631 and a second portion 632, both FIG. 5B, of the filter 215. The first portion 631 of the filter 215 forms a larger angle β with the substrate 40 than does the second portion 632 of the filter 215 (angle α).

In step 1126, the deformation includes pressing against the filter 215 with a tip 612 of a projecting member 610, both FIG. 5B. The tip 612 is supported by the cover 240 via a cantilevered portion 614. This advantageously permits readily controlling angles α and β of FIG. 5B, while maintaining a large open area of the cover aperture 210 to receive the sample 205.

In step 1130, presence or lack of presence of a detectable signal is detected. The detectable signal is sought in a detection zone 56, FIG. 2, disposed along the fluid flow path 64 downstream of the sample addition zone 448. The detection zone 56 includes a detection material responsive to an analyte to produce the detectable signal, as discussed above with reference to FIG. 2. Specifically, the detectable signal corresponds to an amount of the analyte present in the sample. Whether the detectable signal is detected or not, or the strength of the detectable signal as measured, correlate with analyte amounts. Step 1130 can be followed by step 1140 and can include step 1138.

In step 1138, at least one time-based measurement is made to detect the presence or the lack of presence of the detectable signal in the detection zone 56. For example, the detectable signal can be sought in the detection zone 56 a certain amount of time after the sample 205 is added to the device 400. In another example, the detectable signal can be sought periodically, e.g., every 1.5-2.5 seconds, until a large change in signal indicates that a conjugate plume has been detected. Measurements of the detectable signal can then be taken periodically over a selected time, e.g., every 2 seconds for a total of 10 seconds. Further examples of time-based measurements are given in the above-referenced U.S. Patent Application Publication No. 2014/0141527 A1.

In step 1140, a process-related event is triggered based upon the detection of the detectable signal in the detection zone 56. Examples of such events include introducing wash fluid or other reagents to the device 200. Other examples include the removal of the device 400 from an incubator or measurement station.

Figure 12:
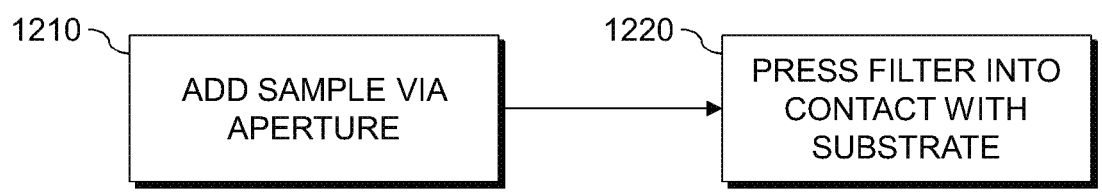

FIG. 12 is a flowchart of a method for controlling filtration or flow characteristics in a lateral-flow assay device such as device 200, FIG. 3, or device 400, FIG. 4. As noted above, the specifically identified components from other figures are exemplary and not limiting, and the steps can be performed in any order unless otherwise indicated. As previously discussed, the device 200 includes a cover 240 and a substrate 40. The cover 240 has an aperture 210 configured to receive a fluidic sample 205, such as whole blood, and peripherally supporting a filter 215. The substrate 40 has a sample addition zone 448 and a fluid flow path 64 through which a filtrate 420 flows under capillary action away from the sample addition zone 448. In various embodiments, the method begins with step 1210.

In step 1210, a selected quantity of a sample 205 is added to the device 200 via the cover aperture 210.

In step 1220, at least one portion of the filter is pressed into contact with the substrate 40 at least partly over the sample addition zone 448 using at least one projecting member 610 of the cover 240. As discussed above, the pressing-into-contact step 1220 can be done during manufacture of the device 200 or at the time of use, and can be done before or after step 1210. As a result of the pressing, at least one angle α is defined, the at least one angle α subtended between the substrate 40 and a hydrophilic portion 429 of the filter 215 spaced apart from the substrate 40 and extending to an edge 230 (outer periphery) of the supported filter 215. The filtrate 420 passes through the filter 215 from the sample 205 at a first flow rate and is retained by capillary pressure in a volume (the peripheral reservoir 425) between the substrate 40 and the hydrophilic portion 429. Also, the filtrate 420 is drawn by capillary pressure from the volume (the peripheral reservoir 425) into the sample addition zone 448 at a second flow rate slower than the first flow rate. The quantity of the sample is based on the first and second flow rates and on the at least one angle. In various aspects, the fluid flow path 64 includes microposts 7, FIG. 1, as noted above. Time-based measurements and process-related events can also be used with this embodiment and are discussed above.

In various embodiments, devices or methods described herein are used with liquids that do not require filtration, e.g., aqueous alcohols or other solvents in which no solute is dissolved. In these embodiments, the peripheral reservoir 425, FIG. 3, can advantageously provide a stable way of storing the fluid, and can permit using a higher percentage of the sample 205 by avoiding latching. Fluidic devices using such fluids and incorporating reservoir 425 can thus be more robust than such devices not incorporating reservoir 425. Moreover, when used with a hydrophilic surface 44, the reservoir 425 can form even in devices that do not include microposts or micropillars. Furthermore, other hydrophilic, porous membranes can be used in place of the filter 215.

| Parts List for FIGS. 1-12: | |
|---|---|
| 1 | assay device |
| 2 | sample addition zone |
| 3 | reagent zone |
| 4 | detection zone |
| 5 | wicking zone |
| 7 | micropost |
| 9 | substrate |
| 20 | lateral-flow assay device |
| 40 | substrate |
| 44 | surface |
| 48 | sample addition zone |
| 52 | reagent zone |
| 55 | detection channel |
| 56 | detection zone |
| 60 | wicking zone |
| 64 | fluid flow path |
| 70 | hydrophilic foil layer |
| 72 | vents |
| 200 | lateral-flow assay device |
| 205 | sample |
| 210 | aperture |
| 215 | filter |
| 220 | meniscus |
| 225 | micropost matrix |
| 230 | edge of filter |
| 235 | welding groove |
| 240 | cover |
| 400 | lateral-flow assay device |
| 416 | filter area |
| 417 | contact area |
| 420 | filtrate |
| 422 | residue |
| 425 | reservoir |
| 427 | contact portion |
| 429 | extending portion |
| 448 | sample addition zone |
| 516 | filter area |
| 517 | contact area |
| 547 | sample zone |
| 548 | sample addition zone |
| 600 | lateral-flow assay device |
| 610 | projecting member |
| 612 | tip |
| 614 | cantilevered portion |
| 628 | portion |
| 631, 632 | portions of filter |
| 648 | sample addition zone |
| 710 | nub |
| 1110, 1120, 1122, 1124 | steps |
| 1126, 1130, 1138, 1140 | steps |
| 1210, 1220 | steps |

The invention is inclusive of combinations of the aspects described herein. References to "a particular embodiment" and the like refer to features that are present in at least one aspect of the invention. Separate references to "an embodiment" or "particular embodiments" or the like do not necessarily refer to the same embodiment or embodiments; however, such embodiments are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted. It will be readily apparent that other modifications and variations are possible within the intended ambits of the concepts described herein and in accordance with the following claims.

The invention claimed is:

1. A lateral-flow assay device for a sample, the device comprising:
   a) a substrate having a sample addition zone and a fluid flow path through which a filtrate flows under capillary action away from said sample addition zone;
   b) a cover arranged over the substrate and having an aperture defining a metering port configured to receive the sample;
   c) a filter having a concave shape and supported peripherally within the aperture and configured to permit at least a portion of the sample to pass therethrough as the filtrate, the supported filter having:
      i) at least one contact portion in direct contact with the substrate to create a contact area that at least partly overlaps the sample addition zone; and
      ii) another portion that extends at an acute angle between the at least one contact portion and the supported periphery of the filter to define a space between the extending portion of the filter and the substrate, the space configured to retain the filtrate by capillary pressure between the substrate and the extending portion of the filter; and
   d) one or more projecting member(s) each including a tip arranged to press the at least one contact portion of the filter against the substrate,
      wherein, when the filtrate passes through the filter, the filtrate forms a reservoir within the space between the extending portion of the filter and the substrate, the reservoir defined by a volume based on the acute angle formed between the substrate and the extending portion of the filter and based on a fluid meniscus of the filtrate, and wherein the filter and sample addition zone are configured to provide a capillary pressure drawing the filtrate from the reservoir to the sample addition zone, and
      wherein the sample addition zone is smaller than the contact area.

2. The device as recited in claim 1, wherein the sample addition zone extends laterally beyond the contact area.

3. The device as recited in claim 1, wherein the contact area extends laterally beyond the sample addition zone.

4. The device as recited in claim 1, wherein the at least one projecting member eccentrically engages a portion of the supported filter.

5. The device as recited in claim 1, wherein at least one of the projecting member(s) comprises a nub.

6. The device as recited in claim 1, wherein at least one of the projecting member(s) includes a cantilevered portion supporting the tip with respect to the cover.

7. The device as recited in claim 1, wherein the substrate includes a plurality of microposts extending upwardly from the surface toward the cover in the sample addition zone, the microposts having heights, diameters and reciprocal spacing between the microposts that induce lateral capillary flow upon the application of filtrate thereto.

8. The device as recited in claim 1, further including at least one reagent zone disposed along the fluid flow path downstream of the sample addition zone, the reagent zone retaining at least one detection material.

9. The device as recited in claim 1, further including a detection zone disposed along the fluid flow path downstream of the sample addition zone and including detection material responsive to an analyte to produce a detectable signal.

10. The device as recited in claim 1, wherein the filter is circular.

11. The device as recited in claim 1, wherein the contact area is smaller than the filter.

12. The device as recited in claim 1, wherein the tip eccentrically engages the filter.

13. The device as recited in claim 1, wherein at least one of the projecting member(s) is arranged to define at least a first portion and an second portion of the filter, the first portion of the filter forming a larger angle with the substrate than does the second portion of the filter.

14. The device as recited in claim 13, wherein the first portion of the filter is upstream of the second portion of the filter with respect to the fluid flow path.

15. The device as recited in claim 1, wherein the filter is defined by an angle extending from the contact portion to an edge of the aperture, the device further comprising at least one engagement feature that controls the angle.

16. The device as recited in claim 15, wherein the engagement feature includes a projecting member.

17. A lateral-flow assay device for a sample, the device comprising:
  a) a substrate having a sample addition zone and a fluid flow path through which a filtrate flows under capillary action away from said sample addition zone;
  b) a cover arranged over the substrate and having an aperture defining a metering port configured to receive the sample;
  c) a filter having a concave shape and supported peripherally within the aperture and configured to permit at least a portion of the sample to pass therethrough as the filtrate, the supported filter having:
     i) at least one contact portion in direct contact with the substrate to create a contact area that at least partly overlaps the sample addition zone; and
     ii) another portion that extends at an acute angle between the at least one contact portion and the supported periphery of the filter to define a space between the extending portion of the filter and the substrate, the space configured to retain the filtrate by capillary pressure between the substrate and the extending portion of the filter; and
  d) one or more projecting member(s) including a tip arranged to press the at least one contact portion of the filter against the substrate,
     wherein, when the filtrate passes through the filter, the filtrate forms a reservoir within the space between the extending portion of the filter and the substrate, the reservoir defined by a volume based on the acute angle formed between the substrate and the extending portion of the filter and based on a fluid meniscus of the filtrate, and wherein the filter and sample addition zone are configured to provide a capillary pressure drawing the filtrate from the reservoir to the sample addition zone.

* * * * *